United States Patent [19]

Baker et al.

[11] Patent Number: 5,103,819
[45] Date of Patent: Apr. 14, 1992

[54] IMPLANTABLE CARDIAC STIMULATOR WITH STATE MACHINE FOR AUTOMATICALLY CONTROLLING GAIN

[75] Inventors: Ross G. Baker, Houston; Joseph W. Vandegriff, Freeport; Drury L. Woodson, Clute, all of Tex.

[73] Assignee: Intermedics, Inc., Angleton, Tex.

[21] Appl. No.: 540,852

[22] Filed: Jun. 20, 1990

[51] Int. Cl.⁵ .......................................... A61N 1/362
[52] U.S. Cl. .......................................... 128/419 PG
[58] Field of Search ............................. 128/419 PG

[56] References Cited

U.S. PATENT DOCUMENTS

| | | | |
|---|---|---|---|
| 4,325,384 | 4/1982 | Blaser et al. | 128/419 PG |
| 4,406,287 | 9/1983 | Nappholz et al. | 128/419 PG |
| 4,768,511 | 9/1988 | DeCote, Jr. | 128/419 PG |
| 4,880,004 | 11/1989 | Baker, Jr. et al. | 128/419 PG |
| 4,913,145 | 4/1990 | Stotts | 128/419 PG |

Primary Examiner—William E. Kamm
Assistant Examiner—Scott M. Getzow
Attorney, Agent, or Firm—John R. Merkling

[57] ABSTRACT

A state machine for automatic gain control of sensing functions in an implantale cardiac stimulator. The state controls sensing levels based on present sensed conditions and on the prior state of the heart. Different rates of adjustment are selected under varying conditions so that the gain level for sense amplifiers can be adjusted without significant overshoot. The state machine comprises a set of four conditions or states together with interconnections or logical paths from one state to another. The rate of adjustment of sense amplifier gain is based on the path traversed in the state machine so that different effective time constants for the control function may be used for different conditions.

26 Claims, 5 Drawing Sheets

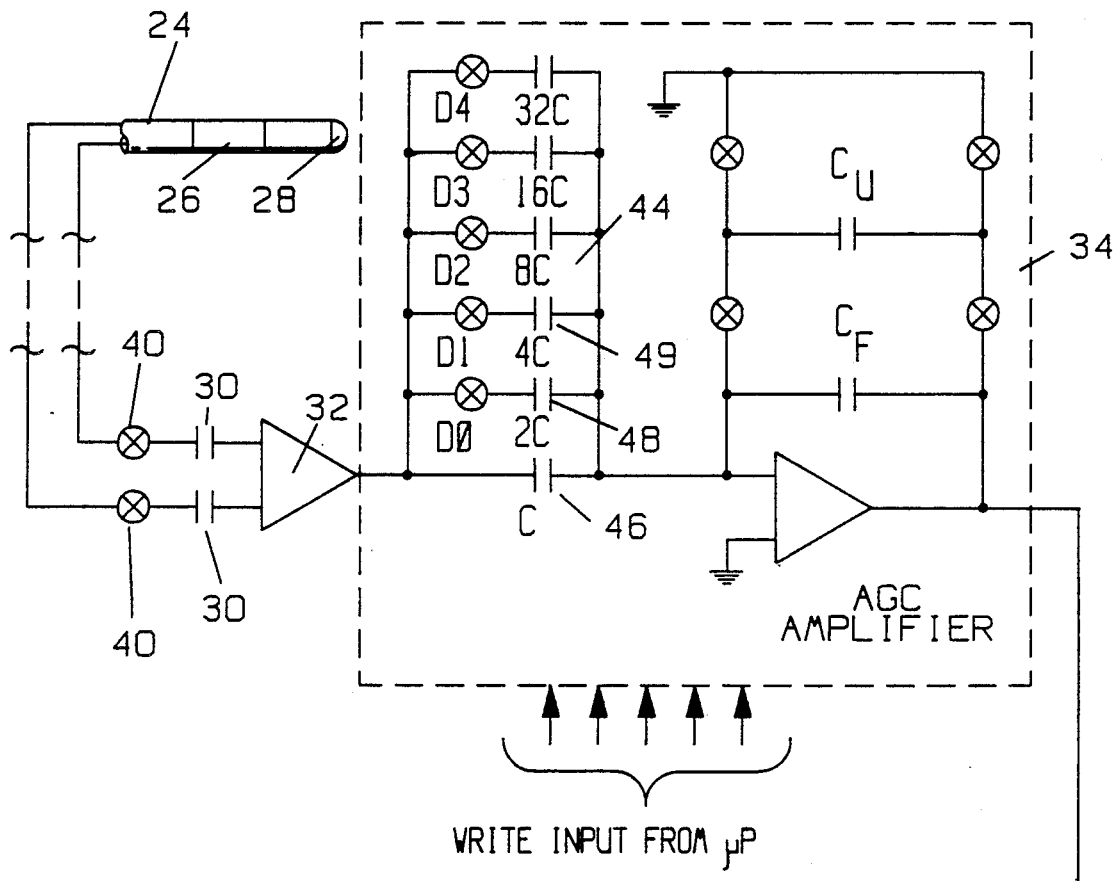
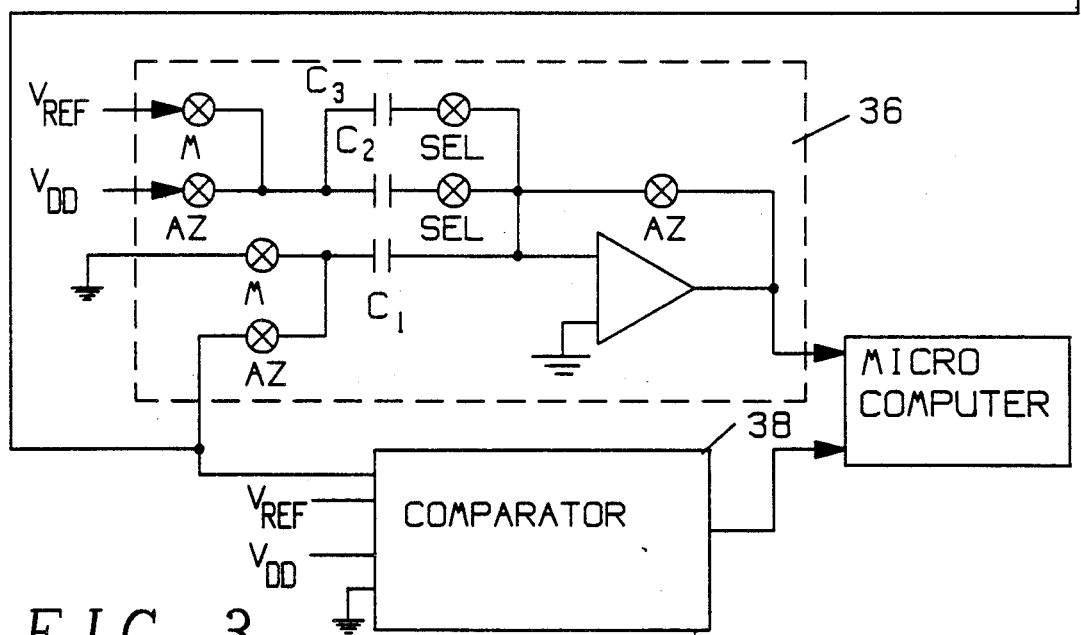
FIG. 3

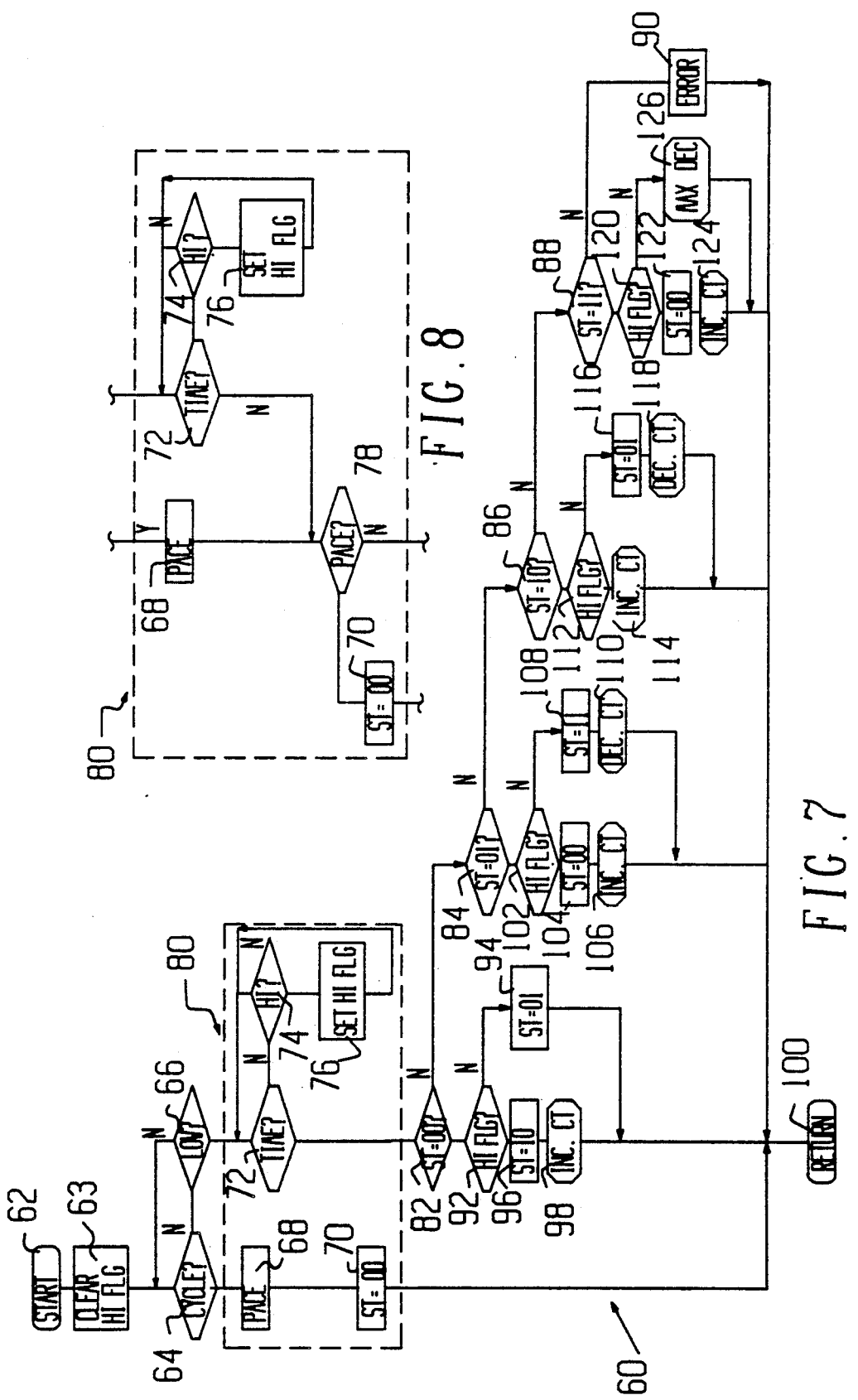

IMPLANTABLE CARDIAC STIMULATOR WITH STATE MACHINE FOR AUTOMATICALLY CONTROLLING GAIN

FIELD OF THE INVENTION

Our invention relates generally to implantable cardiac stimulators such as pacemakers and defibrillators or combinations thereof, and more particularly to automatic gain control for such implantable devices for the purpose of enhancing the capability of the device to sense the condition of a patient's heart for which therapy is to be applied.

BACKGROUND OF THE INVENTION

Arrhythmias are variations in heart rate from the normal sinus rate range of approximately 60 to 120 beats per minute (bpm) prevalent in healthy adult humans with normally functioning hearts. In bradycardia, rates are below 60 bpm, whereas in tachycardia, rates are above 120 bpm. Typically, tachycardia results from physical stress (exercise), emotional stress (excitement), consumption of alcoholic or caffeinated beverages, ingestion of certain drugs such as nicotine, and so forth. The heart rate of a healthy person will gradually return to the sinus rate after removal of the tachycardia-inducing factors. Arrhythmias, however, may require special medical treatment. For example, fibrillation is a high rate arrhythmia characterized by completely uncoordinated contractions of sections of conductive cardiac tissue of the affected chamber of the heart, resulting in a complete loss of synchronous contraction of the overall tissue mass. As a consequence, the chamber stops pumping blood effectively and, in the case of ventricular fibrillation, the lack of oxygenated blood in the tissues leads to death within minutes.

Implantation of a cardiac pacemaker has been a typical procedure of choice for treatment of bradycardia patients. The pacemaker is implanted beneath the skin in the patient's chest and delivers electrical impulses to electrodes positioned at the patient's heart, stimulating the heart to beat at a desired rate in the normal sinus range. Cardiac pacing has also been used in the management of tachyarrhythmia. The heart may be artificially stimulated at a faster than normal pacing rate to terminate a tachycardia or to suppress premature atrial or ventricular contractions which could otherwise lead to supra-ventricular or ventricular tachycardia, flutter, or fibrillation. The pulses delivered to the heart for bradycardia or tachycardia therapy need only be of sufficient magnitude to stimulate the excitable myocardial tissue in the immediate vicinity of the pacing electrode.

More recently, the automatic defibrillator has been proposed for implantation in cardiac patients prone to suffer ventricular or tachycardia fibrillation. The device is adapted to shock the heart with electrical pulses of considerably higher energy content than is delivered in pacing pulses. When fibrillation is detected, one or more high energy "counter-shocks" are applied to the heart to overwhelm the chaotic contractions of individual tissue sections and re-establish organized spreading of action potential from cell to cell of the myocardium, thereby restoring the synchronized contraction of the mass of tissue.

To treat bradycardia, tachycardia, or fibrillation, many cardiac stimulators monitor the electrical activity of the heart. The amplitude of electrical events in the heart varies over a wide range, particularly when events in the ventricle, where the "QRS" complex is generated, are compared to events in the atrium, where the "P" complex is produced. Moreover, the onset of tachycardia may be accompanied by a relatively rapid, sustained change in the amplitude of electrical events. It is important, therefore, for the cardiac stimulator to adapt quickly to changing conditions so that the heart's status can be accurately detected. To accomplish this, some form of automatic gain control in the sensing circuits of the implantable heart stimulator should be provided.

A particular system for utilizing automatic gain control and bandpass filtering in a feedback loop for a defibrillator has heretofore been disclosed in U.S. Pat. No. 4,880,004, which is assigned to the same assignee as our present application, and of which one of us is a co-inventor. Another system for a bradycardia or tachycardia pacemaker has been described in U.S. Pat. No. 4,913,145 (also assigned to our assignee).

There remains a continuing need, however, to improve the response characteristics of automatic gain control, so that accurate sensing can be maintained.

SUMMARY OF OUR INVENTION

We have invented a state machine for automatic gain control of sensing functions in an implantable cardiac stimulator. By using a state machine we can control sensing levels based not only on present sensed conditions but also on the prior state of the heart. This permits different rates of adjustment to be selected under varying conditions so that the gain level for sense amplifiers can be adjusted without significant overshoot.

Our invention comprises a set of four conditions or states of a sequential logical or state machine together with interconnections or logical paths from one state to another. The rate of adjustment of sense amplifier gain is based on the path traversed in the state machine. By using the state machine, different effective time constants for the control function may be used for different conditions.

With the foregoing in mind, it is an object of our invention to provide an implantable cardiac stimulator with automatic gain control governed by a state machine.

A further object of our invention is to provide such automatic gain control whereby the rate of gain adjustment is dependent both on present and prior conditions of the heart.

An additional principal object of our invention is to provide automatic gain control with multiple effective time constants.

Another important object of our invention is to provide a logical decision structure for control of sense amplifier gain in implantable cardiac stimulators.

A further object is to provide a sensing margin related to minimum values of the sensed signal. Yet another object of our invention is to provide sense amplifier gain control which will not be adjusted with respect to post-pace T-waves.

It is also an object of our invention to provide for relatively rapid adjustment of gain control without significant overshoot. These and other objects and features of our invention will become apparent from the following detailed description taken with reference to the accompanying drawings.

DESCRIPTION OF THE DRAWINGS

FIG. 3 is a schematic circuit diagram of an AGC amplifier section of the sense amplifier.

FIG. 7 is a flow chart for implementation of the state machine of FIG. 6.

FIG. 8 is an alternative embodiment for a portion of the flow chart of FIG. 7.

DETAIL DESCRIPTION OF THE PRESENTLY PREFERRED EMBODIMENT

Figure 1:
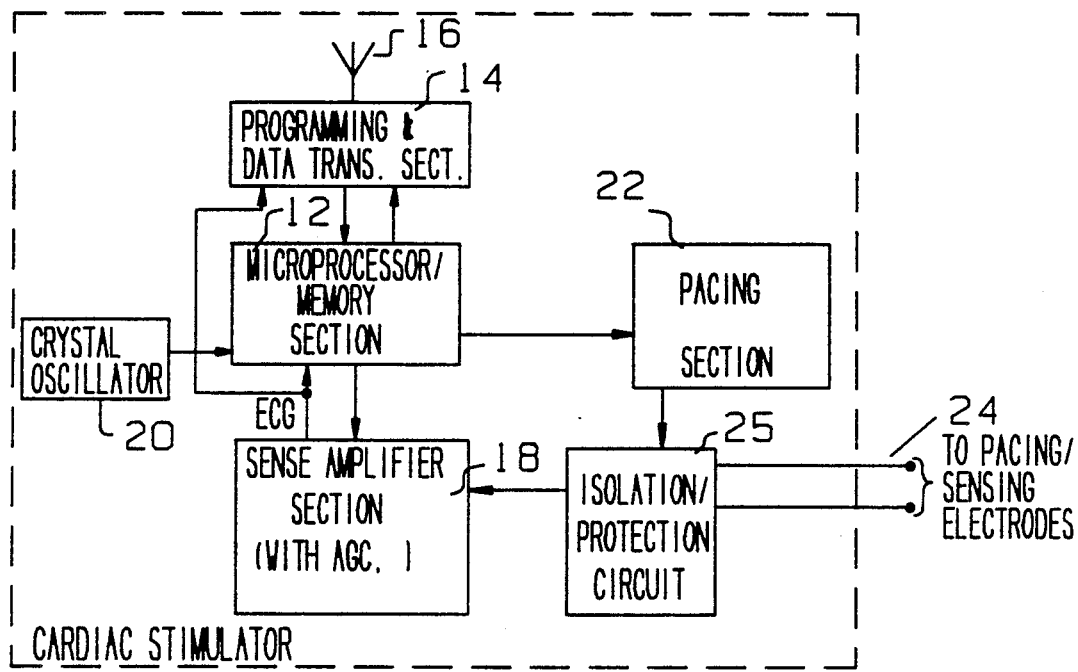
FIG. 1 is a block circuit diagram of an implantable cardiac stimulator, utilizing a sense amplifier having automatic gain control.

We will now describe our presently preferred embodiment of our invention with reference to the accompanying drawings. In the drawings like numerals are used to designate like parts throughout. For clarity we have chosen to describe our invention in connection with a cardiac pacemaker, but it is not limited to that usage and it will be understood that our invention may be utilized in both antitachycardia and bradycardia pacemakers as well as implantable defibrillators.

The cardiac stimulator illustrated in FIG. 1 is adapted to detect preselected aspects of the patient's cardiac activity, and to respond to arrhythmias by generating and managing the delivery of pacing therapies. It will be evident that shock therapies could also be provided to treat fibrillations. The stimulator incorporates circuitry for sensing cardiac activity. The stimulator is assembled and housed in a metal case which is inert to body tissue and fluids. Lead and electrode assemblies for use in sensing cardiac activity and delivering impulses to the patient's heart are separably connectable to the stimulator.

The stimulator includes a digital microprocessor section 12 for storing and executing software instructions and for storing and processing the data for all digital functions of the device (aside from those function which, for purposes of conserving memory capacity, are readily consigned to an external programmer unit). The stimulator 10 also includes an analog system portion for functions involving monitoring of the patient's ECG signal information over each cardiac cycle and enhancing that signal information while reducing noise and other interference through signal filtering and automatic gain control. Other analog functions of the stimulator include developing the respective impulse waveforms to be delivered for therapies, transmitting data between the device and external units such as the programmer and transtelephonic monitoring equipment, and protecting against overloads.

With reference now to FIG. 1, the central microprocessor and memory section 12 of the stimulator processes and stores the data for therapy structures, detection algorithms, and other features. Bidirectionally coupled to microprocessor section 12 is a programming and data transmission section 14 for transmitting data to and from the external programmer and for receiving instructions and monitoring equipment, via an antenna 16. A crystal oscillator 20 is electrically coupled to the microprocessor 12 to provide precise timing signals for system operation.

A sense amplifier section 18, described in detail below, is coupled to the microprocessor section 12 to furnish electrogram signal information and to receive control signals from the microprocessor. The sense amplifier section 18 also supplies electrogram signal information directly to the data transmission section 14 for telemetry to the external monitoring equipment. The sense amplifier section 18 serves as the link to convert electrogram signal information from sensing electrodes (see FIG. 3) attached to the patient's heart into digital information for use by the microprocessor. The microprocessor 12 is in the feedback loop of the sense amplifier section 18 for automatic gain control. The sense amplifier section 18 enhances the electrogram signals and can track the rapidly varying amplitude of certain cardiac signals, for example, in tachycardia or fibrillation episodes.

A pacing section 22 in the cardiac stimulator 10 delivers pacing stimuli to the patient's heart via a pacing lead 24 under the control of the microprocessor 12. Both the sense amplifier section 18 and the pacing section 22 may be protected from electrical surges by an isolution and protection circuit 25. Both must be protected from externally applied defibrillating shocks and the sense amplifier 18 should be isolated from the heart and from the pacing section 22 during pacing.

Figure 2:
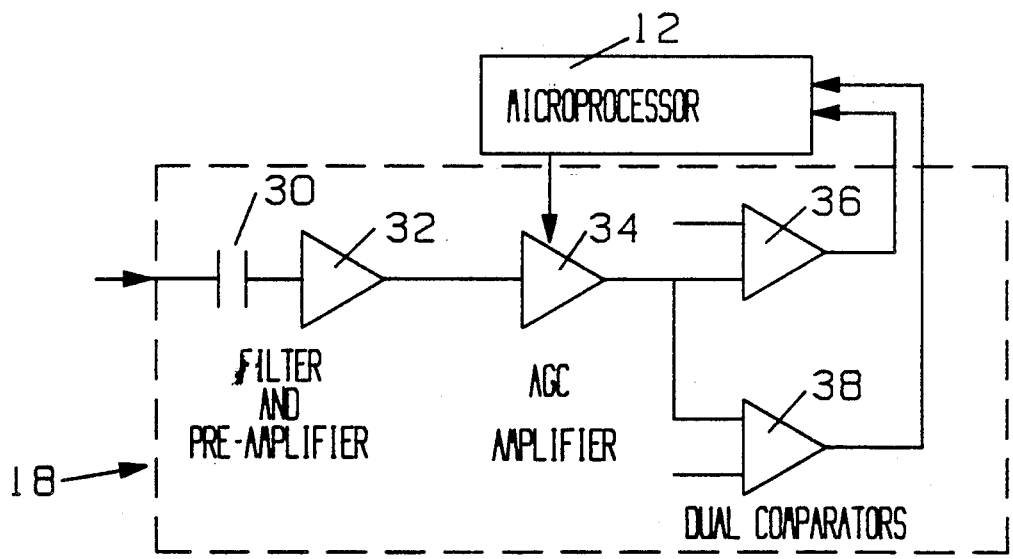
FIG. 2 is a more detailed block circuit diagram of the microprocessor and sense amplifier portion of the cardiac stimulator of FIG. 1.

The sense amplifier section 18 and its relationship to the microprocessor 12 are illustrated in greater detail in FIG. 2. The ECG waveform components detected by the sensing electrodes 26, 28 (see FIG. 3) are applied to high pass filter 30 and a pre-amplifier 32. The waveform is then processed by an automatic gain control (AGC) amplifier 34. The gain of amplifier 34 is automatically controlled by a feedback loop containing a portion of the microprocessor/memory section 12 (FIG. 1). The output of the AGC amplifier 34 is conducted to two comparators. Each comparator 36, 38 compares the output amplitude of the AGC amplifier 34 to a selected outer limit, as will be more fully explained below, and to a selected intermediate level, or sense target, which will also be explained below. One comparator detects positive potentials, while the other detects negative potentials.

The system of FIG. 2 is our preferred embodiment. Our present invention, however, is directed to the control of the AGC amplifier 34. Alternative feedback loops could be used within the scope of our invention.

The illustrated AGC system maintains a preset sensing margin. For a given threshold level on the sense target, this is achieved by adjusting the gain of the AGC amplifier 34 so that the peak voltage seen at the AGC target comparators 36 remains more or less constant. The microprocessor 12 samples the output of the comparators 36, 38 on a cycle by cycle basis. In essence, if the waveform peak exceeds the AGC target (positive or negative) under conditions established by the state machine of our invention, the microprocessor 12 will reduce the gain a small amount. If the waveform peak does not exceed the threshold of the AGC target under other established conditions, it will increase the gain a small amount. The increase or decrease decision process, according to our present invention, will be discussed in more detail later.

The AGC amplifier 34 provides automatic gain control by means of a low current, low voltage switched capacitor amplifier with good transient response as shown in FIG. 3. Referring to FIG. 3, pre-amplifier 32 is a conventional input stage for amplifying the signal representative of cardiac activity of the patient in whom the pacemaker is implanted. The signal is obtained at tip and ring inputs of the cardiac stimulator 10 which are electrically connected to the sensing electrodes 26, 28 of the pacing lead 24. Blanking switches 40 serve to disconnect the inputs during a pace. The output signal of the pre-amplifier 32 is applied to the AGC amplifier 34 which comprises a switched capacitor, highpass amplifier 42, and plurality of switches D0 through D4 controlled by the microprocessor 12. A capacitor $C_F$ is connected in a feedback loop of the amplifier 42. Another capacitor $C_U$ with associated switches is the equivalent circuit of a resistor.

The microprocessor 12 programs the switches D0 through D4 with an array 44 of parallel capacitors, for selective electrical connection of the capacitors in parallel. The ratio of the capacitors in the array 44 is binary weighted, such that capacitor 46 is C, capacitor 48 is 2C, capacitor 50 is 4C, and so forth, the effective capacitance being $C_T(C_{total})$. The flat band gain of the stage is equal to $C_t$ divided by $C_F$ (i.e., $C_T/C_F$), which provides gain control. The effect is a variable gain stage which may be controlled by the microprocessor to provide the desired capacitance values, and thereby the gain. The output signal of stage 34 is a further amplified version of the cardiac signal.

The value of unit capacitor $C_U$, adapted to be selectively connected in the feedback path of amplifier 42, is significant in that it aids in determining the gain versus frequency characteristic of AGC amplifier 34. In particular, the ratio of $C_T$ and $C_F$ together with the unit capacitor and the clock used to set the switches determine the corner of the gain-frequency characteristic. The AGC amplifier 34 blocks DC, but at selected frequencies the amplifier provides reliable signal gain. At the high frequencies of the flat band region of the amplifier, the signal is subjected to a relatively constant gain equal to $C_T/C_F$.

Referring again to FIG. 2, the output signal of the AGC amplifier 34 is fed to the comparators 36, 38 which compare the amplitude of the incoming signal to scaled reference voltages. If the amplitude of the incoming signal from the AGC amplifier 34 is greater than the level of the reference voltage, the comparator generates a logical output. This indicates that the signal amplitude is sufficiently large and is sensed.

The use of switched capacitors in the comparators 36, 38 allows each of the two comparators 36 and 38 to be multiplexed to provide four targets, or voltage reference levels, with two targets provided by each comparator. Comparator 38 is identical to comparator 36, except that the latter is used for establishing and measuring signal voltages and target levels above analog ground whereas the former performs that function below analog ground.

Figure 4:
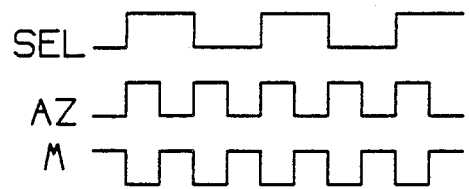
FIG. 4 is a timing diagram.

Referring also to the timing diagram of FIG. 4, the basic comparator 36 operates with two phases consisting of an auto-zero (AZ) phase and a measure (M) phase. The phasing for the switches associated with each comparator is indicated by the AZ and M labels. In one phase the amplifier is auto-zeroed to charge the capacitors C1 and C2 of comparator 36. Capacitor C2 is connected to $V_{DD}$, and capacitor C1 is connected to the input of the comparator stage. Then, immediately prior to the next phase, the measure phase, those capacitors have been charged such that one is relative to analog ground and the other has the input voltage stored on it. Additionally, they also have the offset voltage of the amplifier stored on them. In the measure phase, capacitor C1 is switched to the analog ground point ($V_{AG}$), and capacitor C2 is switched to $V_{REF}$, and therefore the input signal voltage to the comparator relative to the analog ground point will trip the comparator if that voltage is sufficiently above (or below) analog ground. The comparator stage 36 may be viewed as looking at signal levels about analog ground that have been scaled by the ratio C1/(C1+C2).

In each auto-zeroed phase, C1 is charged to $V_{in}$ and C2 is connected to $V_{DD}$, as well as to store the offset voltage. In the following phase, C2 is switched to $V_{REF}$ and C1 is switched to $V_{AG}$. If the voltage on C1 does not change, the voltage seen by the comparator would decrease by an amount equivalent to ratio C1/(C1+C2). If the voltage on C2 does not move, the signal level seen by the comparator would increase. In essence, the comparator is reading $V_{in}$ relative to $V_{DD}$, and $V_{REF}$ relative to $V_{AG}$, and subtracting the two readings. The comparator is utilized to create the zero point and to store all voltage offsets. The $V_{REF}$ to $V_{DD}$ excursion is always the same, and sets a target (in this instance, an inner or lower target) constituting a threshold level based on the ratios of the capacitors (here, C1/C2). When $V_{in}$ is moved up toward $V_{AG}$ in the measure phase, if the voltage at the node being measured returns to become equal to that excursion, the comparator will be tripped.

Figure 5:
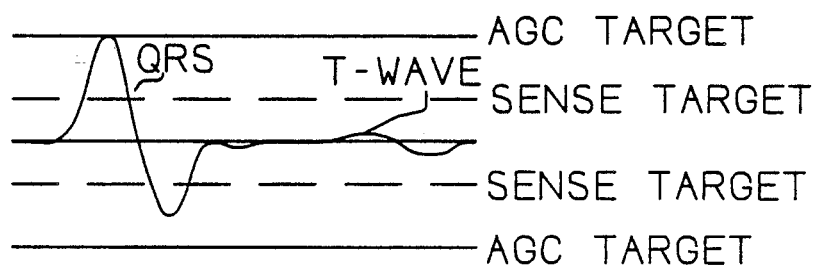
FIG. 5 is a waveform useful for describing the operation of the sense amplifier according to the presently preferred embodiment.

The upper (or outer) target is established and the input voltage (signal level) is compared against it in a similar manner using capacitor C3 in place of C2. C3 is connected to $V_{DD}$ during the auto-zero phase by the switch selection as shown in the timing diagram, at the same time that C1 is connected to the comparator stage input node. Then, in the following measure phase, C1 is switched to analog ground and C3 is switched to the voltage reference. The upper target is therefore established according to the ratio C1/C3. The relationship of the various voltages and signal levels and the target levels in the comparator stage 55 is shown in FIG. 5.

Additional explanation of the control of the comparators can be found in U.S. Pat. No. 4,913,145. The disclosure of that patent is incorporated herein by reference.

During sinus rhythm, the amplitude of the QRS complex dictates the gain setting of the AGC amplifier because of the relatively large amplitude and high frequency content of the QRS. By way of an example of operation, in the presence of a QRS complex which is being monitored by the sense amplifier with its sense and AGC targets, the microprocessor 12 seeks to maintain the gain in such a way that the peak of the signal in the QRS complex approximately crosses the AGC target, as shown in FIG. 5. Such a gain maintenance is achieved in the following manner. Any signal that crosses the sense targets is considered to be a "low crossing". If a low crossing occurs in a cardiac cycle, then sometime after it is sensed a flag is checked (which may, for example, occur during the refractory period, although the precise time is not significant) which indicates whether or not the AGC target was also crossed, called a "high crossing". If the AGC target was crossed, it is an indication that the gain is too high. If the condition continues to meet criteria required by the state machine, the microprocessor decreases the gain in accordance with the logical state machine of our present invention.

The microprocessor also distinguishes cycles in which low crossings occurred but in which there has been no high crossing of the AGC target. If this condition continues to meet criteria set by the state machine, the microprocessor recognizes that the gain is too low and must be increased, as will be explained below.

In order to optimize the automatic gain control of the AGC amplifier 34 by the microprocessor 12, we have invented a state machine to control the rate of gain adjustment. We will explain our invention in connection with a state diagram 50 illustrated in FIG. 6. In our preferred embodiment, four states are defined. These states are named state 00, state 01, state 10 and state 11. State 00 represents the status of the sequential state machine after any pacing event. That is, whenever the implanted cardiac stimulator acts to stimulate the heart, the sequential machine will return to or remain in state 00. As explained above, the cardiac stimulator is capable of detecting an electrical signal in the heart which exceeds a predetermined sense level, as shown in FIG. 5, that is, a low crossing. The cardiac stimulator can also detect an electrical signal in the heart which exceeds an AGC target level that is, a high crossing. State 01 occurs whenever at least one low crossing has been detected without a corresponding high crossing. If a high crossing is detected in the next cycle, the machine returns to state 00. If another low crossing is detected, the machine moves to state 11. Therefore, if the machine is in state 11, at least two consecutive low crossings without corresponding high crossings will have been detected. From state 11, the detection of a high crossing causes the machine to return to state 00. If additional low crossings are detected without high crossings, the machine loops to state 11. A high crossing detected while the machine is in either state 01 or state 11 returns the machine to state 00 and a subsequent high crossing places the machine in state 10. Additional high crossings cause the machine to loop at state 10. In order to control the rate of gain adjustment, the state machine 50 increments or decrements a counter depending on the state of the machine and the detection of low or high crossings.

Our invention is a control mechanism for an implantable cardiac stimulator. For comparison, tradition control systems or feedback loops comprise an input signal, a process, an output signal and a negative feedback path conducting the output signal back to the input. In a typical analog control system, there is a time constant which can be associated with the transient response of the system to a change in the input. In our system the input signal is not continuous but comprises a series of true or false statements dependent upon the occurrence of a low crossing or a high crossing within selected time intervals. The relative maximum of any cardiac waveform is not detected. This feature is known, for example from U.S. Pat. No. 4,880,004, mentioned above. In a discrete control system, such as the one described herein, there is an effective time constant which relates the response of the control system to changes in input conditions. We have discovered that by using a state machine we can assign multiple effective time constants to the control system. In particular, at least two effective constants should be provided. We have found that, in the context of a implantable heart stimulator, for increasing amplitude of detected signal (that is, decreased gain) a long time constant is appropriate. For decreasing signal (that is, increased gain) a shorter time constant is appropriate to avoid loss of signal detection. In our preferred embodiment four time constants are provided: a small positive step to decrease gain, no change or "zero", an intermediate negative step to increase gain and a large negative step to increase gain. Moreover, these factors are applied in combination over a number of cardiac cycles before an actual change in gain is implemented. As a consequence, the state machine creates complex effective time constants within the range from the low decrease step to the high increase step value, dependent upon the detected condition of the heart. Therefore, although a discrete number of effective time constants are implemented in the state machine, the effective overall time constant of the control system can vary almost continuously within a given range. Moreover, the effective overall time constant will change over time in response to the activity of the heart.

Figure 6:
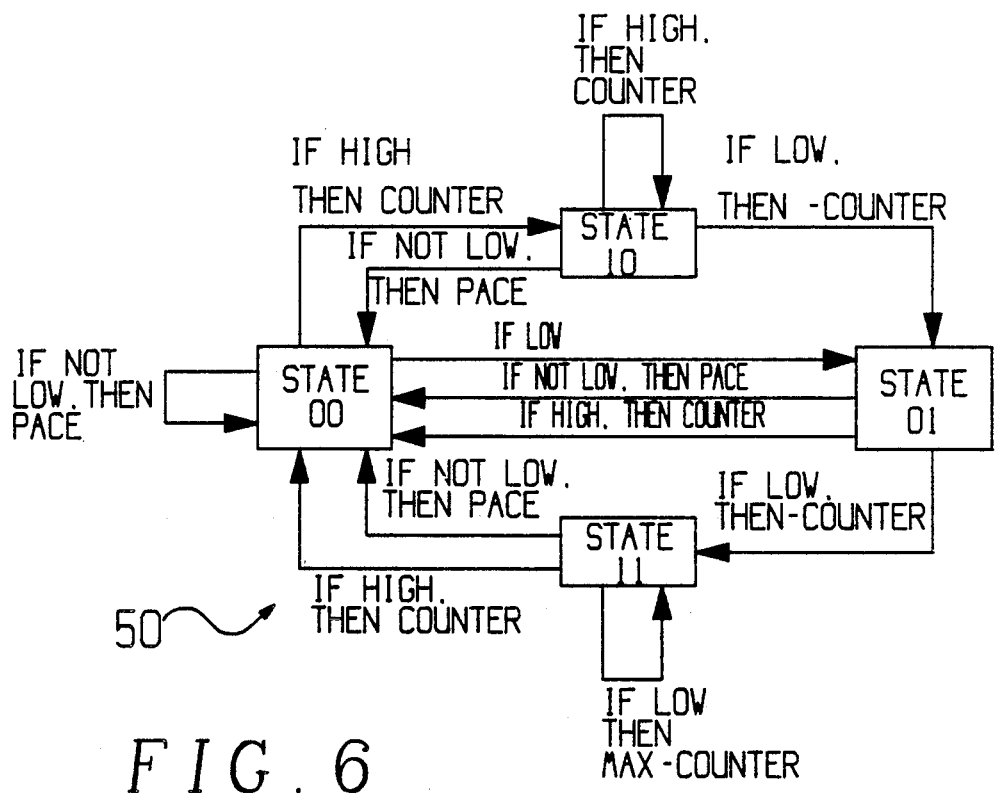
FIG. 6 is a block diagram of a state machine according to our invention.

Another problem for automatic gain control in cardiac stimulators is the erroneous identification of a T-wave as a QRS complex. As shown in FIG. 5, the object of automatic gain control is to amplify the detected QRS complex to the desired AGC target. If the gain is too high, however, the T-wave may cross the sense target and be identified as a low crossing, thereby being falsely identified as a QRS wave. The gain would then be increased even further and improper response by the cardiac stimulator might result. This condition is most likely to occur after the cardiac stimulator has paced the heart because post-pace T-waves are significantly larger than intrinsic T-waves. We have invented and incorporated into the state machine of this invention a mechanism for minimizing this problem. In FIG. 6 it is shown that the state machine 50 returns to state 00 whenever the heart is paced. If gain is unusually high, it is possible that the T-wave resulting from the pace would be detected as a low crossing of a QRS wave. This would set the state machine to 01 and restart the bradycardia period. If the heart is merely in a condition of extreme bradycardia, no true QRS complex will occur in the bradycardia period and the heart stimulator will once again pace the heart. The state machine will return to state 00 without changing a counter. This is the zero effective time constant mentioned above. During pure bradycardia pacing, the state machine can cycle between state 00 and state 01 without attempting to alter the gain in an inappropriate manner.

For further explanation of our invention, we refer now to FIG. 7, which shows a flow chart which illustrates the operation of the microprocessor 12 of FIG. 2. The subroutine 60 is invoked at start 62. A high flag is cleared 63. A preselected bradycardia time cycle is tested 64. Measurement of elapsed time from a given event is well known in this art using timing signals from the crystal oscillator 20, shown in FIG. 2. If the bradycardia period has not elapsed, the microprocessor 12 tests for a low crossing 66. If a low crossing is not detected, the microprocessor 12 cycles through the bradycardia cycle test 64 and the low crossing test 66 until one or the other of the two conditions is fulfilled. If the bradycardia time elapses before a low crossing is detected, the cardiac stimulator will pace 68 the heart and set 70 the state to state 00. If a low crossing is detected 66, a preselected delay period (we prefer 100 milliseconds) is started and the microprocessor 12 tests 72 for the expiration of that period. As long as the delay has not elapsed, the microprocessor 12 will test for a high crossing 74. The microprocessor will cycle between the delay test 72 and the high crossing test 74 until one or the other of the two conditions is fulfilled. If the high crossing test 74 is satisfied, a high crossing flag 76 should be set. After the delay test 72 is satisfied, the microprocessor 12 will then test for the state of the state machine.

It will be recognized by those skilled in the art that conventional details such as clearing flags prior to implementation of the routine 60 have been omitted from this explanation for clarity. In addition, it is possible to perform all changes of state, including step 70, in one subroutine by directing the output of the pace step 68 and of the test 72 to a common test for pacing 78, shown in FIG. 8 as an alternative for the steps in dashed box 80 of FIG. 7. We have preferred to use the embodiment of FIG. 8 for reasons of program structure, but it is not necessary to the implementation of our invention.

After step 72 of FIG. 7, or after step 78 of FIG. 8, the microprocessor 12 begins to test for the state of the state machine 50. In our preferred embodiment, the microprocessor first tests 82 for state 00. If state 00 is not detected, it tests 84 for state 01. If state 01 is not detected, it tests 86 for state 10. Finally, if state 10 is not detected, the microprocessor 12 tests 88 for state 11. This last test is not strictly necessary, since only the four states 00, 01, 10 and 11 are allowed. The failure of all four tests 82–88, however, indicates that an error 90 in the functioning of the microprocessor 12 has occurred.

If state 00 is detected at step 82, the microprocessor 12 tests 92 for a high crossing by detecting the high flag. If no high crossing was detected the state is changed 94 to 01, but no change is made to the counter, the operation of which will be more fully explained below. If a high crossing has been detected, the state is changed to 10 at step 96 and an increment counter subroutine 98 is called. The subroutine 60 is ended at a return 100.

If state 01 is detected 84, the microprocessor 12 again tests 102 for the high flag. If the high flag is detected 102, the state is changed 104 to 00 and the increment counter subroutine is called 106. If the high flag is not detected 102, the state is changed 108 to state 11 and a decrement counter subroutine 210 is invoked. Control of the program passes then to return 100.

If state 10 is detected 86, the microprocessor 12 again tests 112 for the high flag. If the high flag is detected 102, the increment counter subroutine is called 114, but no change of state occurs. If the high flag is not detected the state is changed 116 to 01 and the decrement counter subroutine is called 118. Control of the program then passes to the return 100.

Finally, if state 11 is detected 88, the microprocessor 12 once again tests 120 for the high flag. If the high flag is detected, the state is changed 122 to 00 and the increment counter subroutine is called 124. If the high flag is not detected 120 a maximum decrement counter subroutine is called 126. Control of the program then passes to the return 100. As will be explained below, the effective time constant parameters in our presently preferred embodiment are incorporated in the increment counter subroutine, the decrement counter subroutine, and the maximum decrement counter subroutine, together with a condition of no change to the counter (see step 70 and step 94.)

The increment counter, decrement counter and maximum decrement counter subroutines will now be explained with reference to FIG. 9. Our invention operates by setting a counter to a middle value and then incrementing or decrementing the counter until the counter is either above a designated maximum or below a designated minimum. In our preferred embodiment, a mid-range value of 128 has been chosen, with a maximum value of 255 (FF in hexadecimal) and a minimum value of 0. The gain of amplifier 34 is only adjusted when the counter crosses the minimum or maximum value. It will be recognized, once again, that conventional features known to those skilled in the art, such as providing a ceiling and floor for the values of the counter have been omitted from the following explanation. Although they are not necessary for the implementation of our invention, we prefer to use such features, and they are contained in the accompanying pseudo-code.

Figure 9:
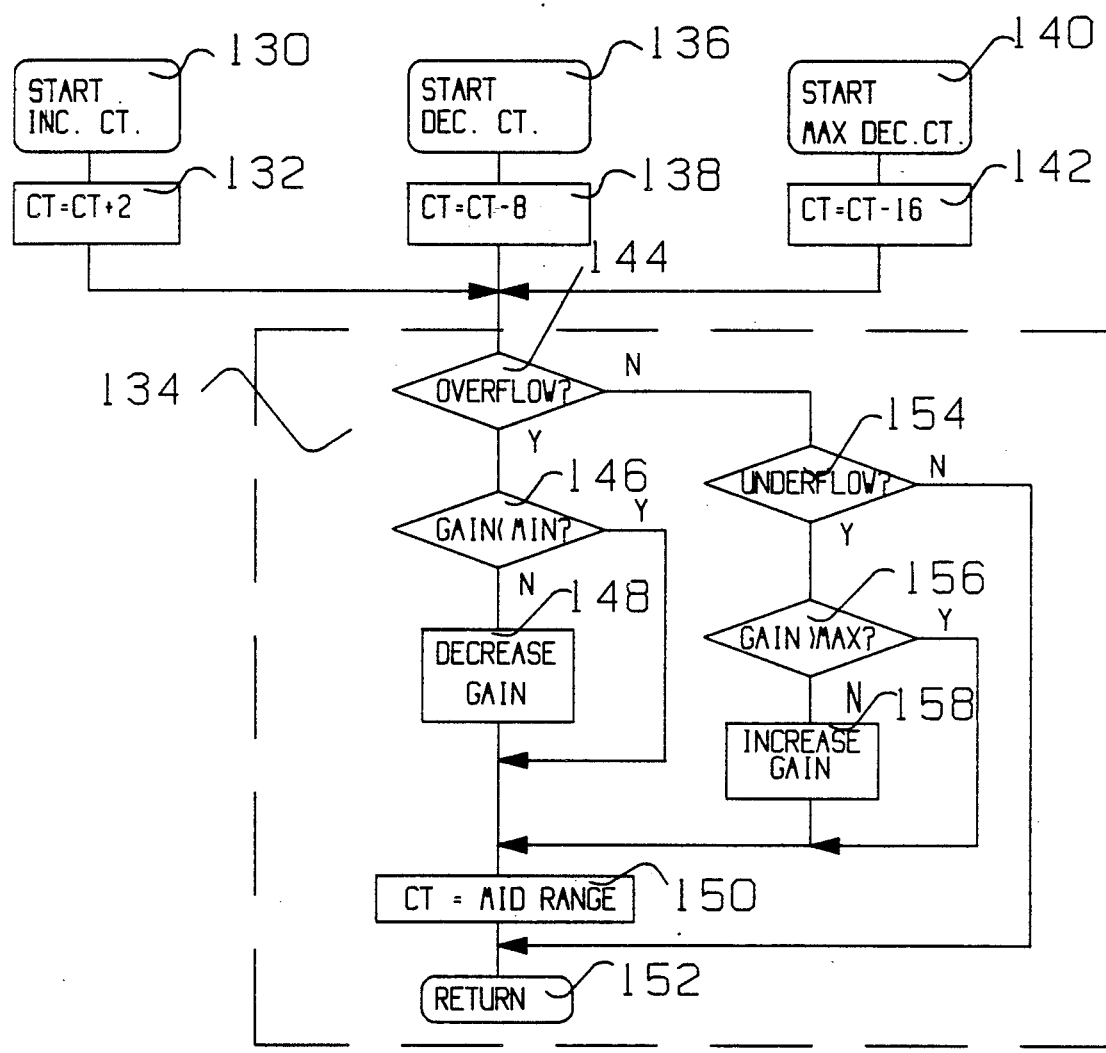
FIG. 9 is a flow chart of a subroutine invoked in the operations illustrated in the flow chart of FIG. 7.

It can been seen from FIG. 9 that the increment counter, decrement counter and maximum decrement counter subroutines have much of their code in common. If the increment counter subroutine is invoked at start increment counter 130, the value of the counter is increased 132. In our preferred embodiment, it is increased by a value of two. This value represents one of the effective time constant parameters that can be selected for the implementation of our invention. It is also one of the boundary values since it represents a limit to the rate at which the gain can be decreased in response to increasing signal magnitude. After the counter has been increased, control then passes to the common steps 134, which will be explained more fully hereafter.

In order of magnitude, the next effective time constant for our invention is 0, that is, no change to the counter. This effective time constant is employed at steps 70 and 94 where no change in the counter occurs, although there is a change in state in the state machine. However, additional steps are not needed to implement the zero time constants.

The decrement counter subroutine begins at the start decrement counter step 136. The counter is then decremented 138 by a selected intermediate amount. In our preferred embodiment, this value is 8. This represents the third effective time constant in the state machine 50 of FIG. 6. It can been seen that this intermediate time constant will be employed at most twice in a sequence passing from state 10 through state 01 to state 11. The increase counter subroutine and the maximum decrease counter subroutine, on the other hand, can be invoked many times until the maximum or minimum value of the counter have been reached. After the counter has been decremented 138, the common steps 134 are implemented.

The maximum decrement counter subroutine is invoked at start maximum decrement counter 140. The counter is then decreased by a relatively large second amount 142. In our preferred embodiment, this value is 16. This is the fourth effective time constant in our system. It also represents a boundary on the rate at which the gain of the amplifier 60 can be increased in response to decreasing signal amplitude. After the counter is decreased 142, control is passed to the common steps 134, which we will now explain.

In the common steps 134, the microprocessor 12 first tests 144 for overflow. In the present embodiment, that implies that the counter is equal to or greater than 256. If an overflow has occurred, there have been too many high crossings detected and the gain must be decreased. The microprocessor 12 first tests 146 to be sure that the gain is greater than a predetermined minimum gain. If the gain is above the minimum, the gain is decreased 148, the counter is set 150 to the mid-range and control is returned 152 to the point where the subroutine was invoked.

If an overflow is not detected 144, the microprocessor 12 tests for an underflow 154. In our embodiment, this implies that the counter is less than 0. If neither and underflow nor an overflow is detected, the program returns 152 without increasing or decreasing the gain. As will be explained more fully hereafter, more than one cardiac cycle is necessary before the gain will be adjusted. This permits the four effective time constants to be combined so that the overall effective time constant of the control system can continually vary from a maximum to a minimum time constant in response to the detected condition of the heart. If an underflow is detected 154, the microprocessor 12 tests 156 to determine the gain of the amplifier 34 is less than a predetermined maximum. If a gain is less than the maximum, the microprocessor 12 increases 158 the gain. The counter is then set to the mid-range 150 and program control is returned 152.

We have previously stated that multiple cardiac cycles are necessary before the gain of the amplifier 34 will be increased or decreased. By way of example consider the state machine 50 of FIG. 6 with the state at 00. Further assume that the gain is very high so that the QRS wave will have both a low and high crossing. The counter will be at 128 initially. In response to the detected high crossing, the state will change from 00 to state 10 and the counter will be incremented by two (step 132). There will be neither an overflow (step 144) nor an underflow (step 154) and the gain of the amplifier 34 will not be adjusted. In the next cycle, assuming that the detected cardiac waveform has been constant, the state will not change, but will remain state 10 and the counter will again be incremented by two. This will continue until the counter equals or exceeds 256, that is, a minimum of 64 cycles. If the intrinsic heart rate is between 60 and 70 beats per minute this implies an elapsed of about a minute. This represents the minimum period between decreases in gain in our present invention. Of course, these values are illustrative only and can readily can be changed without departing from the teachings of our invention.

Next we will consider a situation in which the gain is too low and needs to be increased. Referring again to FIG. 6, if the state machine 50 is in state 00, and the counter is initially at the mid-range value of 128, a low crossing without an associated high crossing will change the state from 00 to state 01. The counter, however, will not change, thus invoking the "zero" or second effective time constant of our invention. In the next cycle, if a low crossing is again detected without a corresponding high crossing the state is changed to 11 and the counter is decremented by the intermediate value (in our illustrated embodiment 8) thus invoking the third effective time constant. In the next and subsequent cycles, if a low crossing is detected without a corresponding high crossing, the counter will be decremented by the highest value, in our example, by 16. This invokes the fourth effective time constant of our invention. An underflow condition occurs after 10 cycles and the gain of the amplifier 34 will be increased. The elapsed real time is on the order of ten seconds. Therefore, in our preferred embodiment, the gain can be increased much faster than it can be decreased. Moreover, within these limiting examples, the multiple time constants may be combined in different ways from cycle to cycle to produce overall effective time constants which vary above a minimum value depending on the condition of the heart.

The following pseudo code represents our implementation of our invention.

```
Auto_Sense Adjust
If outer target not crossed
Then
        Clear outer target crossed bit
Endif
If Auto_Sensing ON
Then
    Cases of Sense_State
        Sense_State == 00
            If outer target crossed
            Then
                    Sense_State = 10
                    GoTo INCREMENT_COUNTER
            Else
                    Sense_State = 01
                    RETURN ... EXIT
            Endif
        Sense_State == 01
            If outer target crossed
            Then
                    Sense_State = 00
                    GoTo INCREMENT_COUNTER
            Else
                    Sense_State = 11
                    GoTo DEC_CTR
            Endif
        Sense_State == 10
            If outer target crossed
            Then
                    GoTo INCREMENT_COUNTER
            Else
                    Sense_State = 01
                    GoTo DEC_CTR
            Endif
        Sense_State == 11
            If outer target crossed
            Then
                    Sense_State = 00
                    GoTo INCREMENT_COUNTER
            Else
                    GoTo DEC_CTR_x2
            Endif
    End of Cases of Sense_State
INCREMENT_COUNTER
        Sense_Counter += 2
        If Overflow
        Then
                Sense_Counter = 00
        Endif
        GoTo TEST_COUNTER
DEC_CTR_x2
        Sense_Counter -= 16
        GoTo DC1
DEC_CTR
        Sense_Counter -= 8
DC1
        If Underflow
        Then
                Sense_Counter = FF
        Endif
        GoTo TEST_COUNTER
TEST_COUNTER
        If Sense_Counter Overflowed
        Then
                If Gain > Hardware Minimum
                Then
                        Decrease Gain 1 step
                Endif
        Else
                If Sense_Counter Underflow
```

```
                    -continued
                  Auto_Sense Adjust
              Then
                    If Gain < Hardware Maximum
                    Then
                          Increase Gain 1 step
                    Endif
                    Else RETURN ... EXIT
              Endif
         Endif
         Reset Sense_Counter to 128
End Auto_Sense_Adjust
```

Our invention may be embodied in other specific forms without departing from the spirit or essential characteristics thereof. The present embodiment is therefore considered in all respects to be illustrative and not restrictive, the scope of the invention being indicated by the appended claims rather than the foregoing description and all changes which come within the meaning and range of equivalency of the claims are therefore intended to be embraced therein.

We claim as our invention:

1. An apparatus for use in a cardiac stimulator comprising
    means for detecting a signal representative of cardiac activity;
    means for amplifying the detected signal; and
    means responsive to the detected signal for selectively varying the amplification gain thereof, said gain varying means comprising means for applying a plurality of discrete effective time constants to alter a rate at which the amplification gain is varied and means for selecting an effective time constant based on a prior condition of the detected signal and on a present condition of the detected signal.

2. The apparatus according to claim 1 wherein the time constant applying means further comprise means for serially combining selected time constants from said plurality of time constant to produce a continuous range of effective time constants.

3. The apparatus according to claim 2 wherein the time constant applying means comprise means for increasing the application gain at a selected rate and means for decreasing the amplification gain at a second, relatively slower rate.

4. The apparatus according to claim 3 wherein the time constant applying means comprise a logical state machine.

5. The apparatus according to claim 4 wherein said logical state machine further comprises a plurality of states and means for passing from one state to another in response to the detected signal.

6. The apparatus according to claim 5 wherein the plurality of states comprise four states.

7. An apparatus for use in a cardiac stimulator comprising
    means for detecting a signal representative of cardiac activity;
    means for amplifying the detected signal, means responsive to the detected signal for selectively varying the amplification gain thereof, said gain varying means comprising
        means for recording a condition of said detected signal during at least one prior cardiac cycle;
        means for detecting a present condition of said detected signal; and
        means for selecting a rate of change of said amplification gain dependant on said recorded and said present conditions.

8. The apparatus according to claim 7 wherein the rate selecting means further comprise a plurality of preselected discrete rates and means for serially combining said discrete rates to produce a continuous range of rates of change.

9. The apparatus according to claim 8 wherein the rate selecting means comprise means for increasing the amplification gain at a selected rate and means for decreasing the amplification gain at a second, relatively slower rate.

10. The apparatus according to claim 7 further comprising means for accumulating said condition of said signal over a series of cardiac cycles and means for identifying a first accumulated condition indicative of increasing amplification gain and for identifying a second accumulated condition indicative of decreasing amplification gain.

11. The apparatus according to claim 10 wherein the accumulating means further comprise means for weighting said condition to favor either increasing amplification gain or decreasing amplification gain.

12. The apparatus according to claim 11 wherein the condition accumulating means comprise a logical state machine.

13. The apparatus according to claim 12 wherein said logical state machine further comprises
    a plurality of states,
    a plurality of path means for passing from one state to another in response to the detected signal, each path comprising a discrete factor, and
    means for summing said discrete factors wherever said state machine passes from one state to another, and wherein said condition identifying means is responsive to said discrete factor summing means.

14. The apparatus according to claim 13 wherein the plurality of states comprise four states.

15. A method for controlling amplification gain in a cardiac stimulator comprising
    detecting a signal representative of cardiac activity;
    amplifying the detected signal;
    selecting an effective time constant from a plurality of discrete effective constants based on a prior condition of the detected signal;
    applying said selected effective time constants to alter a rate at which the amplification gain is varied; and
    selectively varying the amplification gain thereof.

16. The method according to claim 15 wherein the step of applying time constants further comprises serially combining selected time constants from said plurality of time constants to produce a continuous range of effective time constants.

17. The cardiac method according to claim 16 wherein the step of applying time constants comprises
    increasing the amplification gain at a selected rate,
    and decreasing the amplification gain at a second, relatively slower rate.

18. The method according to claim 17 wherein the step of serially combining said selected time constants comprises passing from one state to another in response to the detected signal in a logical state machine.

19. A method for controlling amplification gain in a cardiac stimulator comprising
    detecting a signal representative of cardiac activity;
    amplifying the detected signal, recording a condition of said detected signal during at least one prior cardiac cycle;

detecting a current condition of said detected signal;

selecting a rate of change of said amplification gain dependant on said recorded and said current conditions, and selectively varying the amplification gain.

20. The method according to claim 19 wherein the rate selecting step further comprises serially combining at least some of a plurality of preselected discrete rates to produce a continuous range of rates of change.

21. A method according to claim 20 wherein the rate selecting step comprises increasing the amplification gain at a selected rate and decreasing the amplification gain at a second, relatively slower rate.

22. The method according to claim 19 further comprising accumulating said selected condition of said signal over a series of cardiac cycles, identifying a first accumulated condition indicative of increasing amplification gain, and identifying a second accumulated condition indicative of decreasing amplification gain.

23. The method according to claim 22 wherein the condition accumulating step further comprises weighting said selected condition to favor either increasing amplification gain or decreasing amplification gain.

24. The method according to claim 23 wherein said condition accumulating step further comprises passing from one of a plurality of states to another along a logical path in response to the detected signal, each path comprising a discrete factor, summing said discrete factors wherever said state machine passes from one state to another, and responding to said summing means to identify said accumulated condition.

25. An appartus for use in a cardiac stimulator comprising means for detecting a signal representative of cardiac activity;

means for applying the detected signal; and means responsive to the detected signal for selectively varying the amplification gain thereof, said gain varying means comprising means for applying at least two discrete effective time constants, at least two of said time constants being of different absolute value, to alter a rate at which the amplification gain is varied.

26. A method for controlling amplification gain in a cardiac stimulator comprising detecting a signal representative of cardiac activity;

amplifying the detected signal;

selecting a discrete effective time constant from a group of at least two discrete effective time constants, at least two of said time constants being of different absolute value;

applying said selected time constant to alter a rate at which the amplification gain is varied; and selectively varying the amplification gain thereof.

* * * * *